(12) United States Patent
Li et al.

(10) Patent No.: US 10,323,046 B2
(45) Date of Patent: Jun. 18, 2019

(54) METHOD FOR PREPARING L-BPA

(71) Applicant: NEUBORON MEDTECH LTD., Nanjing, Jiangsu (CN)

(72) Inventors: Shihong Li, Jiangsu (CN); Jing He, Jiangsu (CN); Yuanhao Liu, Jiangsu (CN); Zheng Wang, Jiangsu (CN)

(73) Assignee: NEUBORON MEDTECH LTD., Nanjing, Jiangsu (CN)

( * ) Notice: Subject to any disclaimer, the term of this patent is extended or adjusted under 35 U.S.C. 154(b) by 0 days.

(21) Appl. No.: 15/886,221

(22) Filed: Feb. 1, 2018

(65) Prior Publication Data

US 2018/0155368 A1 Jun. 7, 2018

Related U.S. Application Data

(63) Continuation of application No. PCT/CN2016/094881, filed on Aug. 12, 2016.

(30) Foreign Application Priority Data

Aug. 14, 2015 (CN) .......................... 2015 1 0498779

(51) Int. Cl.
*C07F 5/02* (2006.01)
*C07B 41/08* (2006.01)
*C07B 47/00* (2006.01)
*C07B 63/00* (2006.01)
*C07F 3/02* (2006.01)

(52) U.S. Cl.
CPC .............. *C07F 5/025* (2013.01); *C07B 41/08* (2013.01); *C07B 47/00* (2013.01); *C07B 63/00* (2013.01); *C07F 5/02* (2013.01); *C07F 3/02* (2013.01); *Y02P 20/55* (2015.11)

(58) Field of Classification Search
CPC ......... C07B 41/08; C07B 47/00; C07B 63/00; C07F 3/02; C07F 5/02; C07F 5/025; Y02P 20/55
See application file for complete search history.

(56) References Cited

U.S. PATENT DOCUMENTS

| 5,157,149 A | 10/1992 | Samsel |
| 8,765,997 B2 | 7/2014 | Shaw et al. |
| 2013/0331599 A1 | 12/2013 | Shaw et al. |

FOREIGN PATENT DOCUMENTS

| CN | 10447823 | * | 3/2015 |
| CN | 104447822 A | | 3/2015 |
| CN | 104447823 A | | 3/2015 |
| CN | 104961756 | * | 10/2015 |
| CN | 104961756 A | | 10/2015 |
| EP | 2851362 | * | 3/2015 |
| EP | 2865682 A1 | | 4/2015 |

OTHER PUBLICATIONS

CN10447823 translated (Year: 2015).*
Wang et al. (Noncryogenic I/Br—Mg Exchange of Aromatic Halides Bearing Sensitive Functional Groups Using i-PrMgCl-Bis[2-(N,N-dimethylamino)ethyl] Ether Complexes, Organic Letters 8(2), pp. 305-307, published 2006) (Year: 2006).*
Ousmer et al. (Gram-Scale Preparation of a p-(C-Glucopyranosyl)-L-phenylalanine Derivative by a Negishi Cross-Coupling Reaction, Eur. J. Org. Chem., 1216-1221 Published 2006) (Year: 2006).*
Extraction acid base, (Published 2008) (Year: 2008).*
Grignard, (Published 2013) (Year: 2013).*
CN104961756 translated (Year: 2015).*
Wang et al. 2005 (Addition of Grignard Reagents to Aryl Acid Chlorides: An Efficient Synthesis of Aryl Ketones Organic Letters 7(25), pp. 5593-5595, published 2005) (Year: 2005).*
Hidekazu Nakao et al., Asymmetric Synthesis of Optically Pure L-p-Boronophenylalanine by a Hybrid Process, Bioscience, Biotechnology, and Biochemistry, 1996, 60(4), 683-684.
Hiroyuki Nakamura et al., A Practical Method for the Synthesis of Enantiomerically Pure 4-Borono-L-phenylalanine, 2000, Bull. Chem. Soc. Jpn., 73, 231-235.

(Continued)

*Primary Examiner* — Yevgeny Valenrod
*Assistant Examiner* — Blaine G Doletski
(74) *Attorney, Agent, or Firm* — Tim Tingkang Xia, Esq.; Locke Lord LLP

(57) ABSTRACT

Provided is a method for preparing L-BPA, which includes steps of:
reacting N-protected (S)-4-halophenylalanine of Formula I, a boronating agent, Grignard reagent and bis(2-dimethylaminoethyl)ether to obtain a reaction mixture, wherein the reaction mixture comprises N-protected (S)-4-boronophenylalanine of Formula II and the $R^2$ group represents a protecting group;

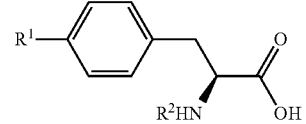

Formula I

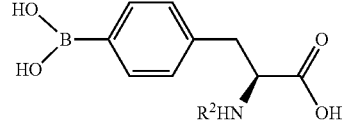

Formula II

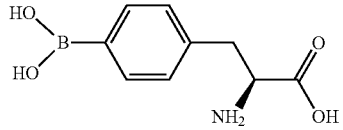

Formula III isolating the N-protected (S)-4-boronophenylalanine from the reaction mixture; and
deprotecting the $R^2$ group of the N-protected (S)-4-boronophenylalanine to obtain L-BPA, wherein the L-BPA has a structure of Formula III.

17 Claims, No Drawings

(56) References Cited

OTHER PUBLICATIONS

Christophe Malan et al., A Concise Preparation of 4-Borono-L-phenylalanine (L-BPA) from L-Phenylalanine, J. Org. Chem., 1998, 63, pp. 8019-8020.
Igor B. Sivaev et al., L-4-Boronophenylalanine (all around the one molecule), Issue in Honor of Prof. Irina Beletskaya, 2008, pp. 47-61.
Xiaoya Zhao et al., Recent Progress of Grignard Reagent on its Synthesis, Activity Regulation and Selective Reactions, China Academic Journal Electronic Publishing House, 2014, vol. 36 No. 6, pp. 481-487.
Christophe Malan et al., Synthesis of 4-Borono-L-phenylalanine, SYNLETT, 1996, pp. 167-168.
Falk Wienhold et al., Synthesis of Functionalized Benzoboroxoles for the Construction of Boronolectins, Synthesis, 2011(24), 4059-4067. pp. 4059-4067.

\* cited by examiner

METHOD FOR PREPARING L-BPA

RELATED APPLICATIONS INFORMATION

This application is a continuation of International Application No. PCT/CN2016/094881, filed on Aug. 12, 2016, which claims priority to Chinese Patent Application No. 201510498779.9, filed on Aug. 14, 2015, the disclosures of which are hereby incorporated by reference.

FIELD OF THE DISCLOSURE

The present disclosure relates generally to a method for preparing boron containing drug for boron neutron capture therapy, and, more particularly, to a method for preparing L-BPA.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for Embodiment, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. The two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

BNCT is also well known for binary cancer therapy, for its effectiveness depending on the concentration of the boronated pharmaceuticals and the number of the thermal neutrons at the tumor site. Thus, besides improvement of flux and quality of the neutron source, the development of the boronated pharmaceuticals plays a significant role in BNCT researches.

It is known at present that, 4-($^{10}$B)borono-L-phenylalanine (L-$^{10}$BPA) is an important boron containing drug for BNCT.

Therefore, various methods for the synthesis of L-BPA have been developed now. As shown in the following Formula (A), two synthesis approaches of L-BPA including formation (a) and formation (b) have been developed.

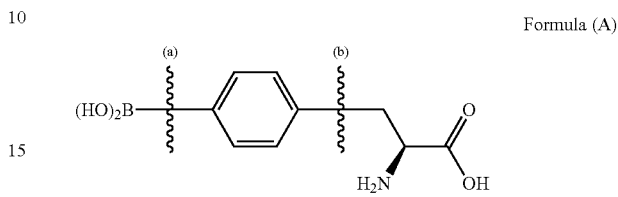

Formula (A)

The approach demonstrated as formation (a) is by introduction of boronic acid group into phenylalanine, which is based on forming the C—B bond directly by the introduction of the dihydroxylboryl substituent to the phenylalanine fragment.

*J. Org. Chem.* 1998, 63, 8019 discloses a method undergoing palladium-catalyzed cross-coupling between an amine-protected L-4-iodophenylalanine, such as (S)—N-Boc-4-iodophenylalanine, and a diboron compound, such as bis-(pinacolato)diboron. L-BPA is then obtained after removal of the protecting group of amine and boronic acid of the phenylalanine.

However, an additional pre-method is further required for preparing the boronating agent, resulting in more time consumption and complicacy of the method, and thereby failing to prepare L-BPA in high yield. The prior art discloses that the carboxylic acid of (S)—N-Boc-4-iodophenylalanine reactant is protected into benzyl ester to improve the yield of the obtained protected L-BPA up to 88%. However, an additional step of removing the benzyl ester protecting group of the carboxylic acid of the protected L-BPA is further needed, which complicates the synthetic method.

Accordingly, the drawbacks of this method also include the additional pre-method for preparing the boronating agent as mentioned above, and further include the time-consuming and multi-step synthesis involving the protection step of the carboxylic acid and the deprotection step of the carboxylic acid afterwards.

Another approach demonstrated as formation (b) involving coupling reaction between an amino acid and a boron-containing benzyl or benzaldehyde fragment is also developed.

*Biosci. Biotech. Biochem.* 1996, 60, 683 discloses an enantioselective synthesis of L-BPA by coupling cyclic ethers of boronic acid and a chiral derivative from L-valine, wherein the cyclic ethers of boronic acid are prepared from 4-boronobenzylbromide in advance. However, the last synthetic step of the method readily results in undesired racemization of the amino acid. Thus, an enzymatic resolution step, which typically reduces the production yield, is required to obtain optically-pure L-BPA.

Accordingly, the drawbacks of this method still include the additional pre-method for preparing the boronating agent, resulting in more time consumption and complicacy of the method, and thereby failing to prepare L-BPA in high yield.

Besides, $^{10}$B contained in L-BPA is known as the critical factor accumulated in tumor cells and subsequently irradiated with thermal neutron. Thus $^{10}$B renders L-BPA a treatment of cancer through boron neutron capture therapy (BNCT).

However, natural boron exists as 19.9% of $^{10}$B isotope and 80.1% of $^{11}$B isotope. Therefore, many researchers have been developing synthetic methods suitable for producing L-BPA, and preferably suitable for producing $^{10}$B-enriched L-BPA.

As disclosed in *J. Org. Chem.* 1998, 63, 8019 mentioned above, the conventional methods comprise multi-step syntheses of the boronating agents, which reduce a large amount of $^{10}$B-enriched materials during the method. As a result, the methods are not suitable for producing $^{10}$B-enriched L-BPA.

As disclosed in *Biosci. Biotech. Biochem.* 1996, 60, 683 mentioned above, an optically pure L-BPA is not obtained until the enzymatic resolution step, and also the multi-step syntheses of the boronating agent render the transformations of the $^{10}$B-enriched materials during the method. Hence, the conventional method is not suitable for producing $^{10}$B-enriched L-BPA as well.

Furthermore, *Bull. Chem. Soc. Jpn.* 2000, 73, 231 discloses a method based on coupling 4-iodo-L-phenylalanine and pinacolborane in the presence of palladium catalyst. However, since the prior art is silent on how to produce $^{10}$B-enriched L-BPA and also $^{10}$B-enriched pinacolborane is not commercially available, the method is not suitable for producing $^{10}$B-enriched L-BPA, either.

In addition, *Synlett.* 1996, 167 discloses a method by coupling iodophenylborate and L-serine zinc derivatives. The method involves indispensable pre-preparation of the L-serine zinc derivatives and the pre-preparation of the iodophenylborate, thereby giving a low yield of L-BPA. Besides, the method is still not suitable for producing $^{10}$B-enriched L-BPA, for both $^{10}$B-enriched $BI_3$ and 1,3-diphenylpropane-1,3-diol adopted in the method are not commercially available.

The statements in this section merely provide background information related to the present disclosure and may not constitute prior art.

SUMMARY

Given that the drawbacks of the prior art such as large time consumption, multi-steps and additional pre-method for preparing the boronating agents, an aspect of the present disclosure is to develop a timesaving, efficient, cost effective, and environmentally friendly method for preparing L-BPA without tedious purification. Accordingly, L-BPA prepared by the method of the disclosure has high chemical purity and high optical purity.

Another aspect of the present disclosure is to develop a method for preparing L-$^{10}$BPA, particularly, a method for preparing L-$^{10}$BPA that is timesaving, efficient, cost effective, environmentally friendly, convenient and without tedious purification. The method in accordance with the present invention is effective in producing L-$^{10}$BPA with high chemical purity, high optical purity and high isotopic purity.

Another aspect of the present disclosure is to develop a method both suitable for preparing L-BPA and L-$^{10}$BPA; particularly, a method for preparing both L-BPA and L-$^{10}$BPA that is timesaving, efficient, cost effective, environmentally friendly, convenient and without tedious purification.

Accordingly, the method in accordance with the present disclosure includes steps of: reacting N-protected (S)-4-halophenylalanine of Formula I, a boronating agent, Grignard reagent and bis(2-dimethylaminoethyl)ether to obtain a reaction mixture, wherein the reaction mixture includes N-protected (S)-4-boronophenylalanine of Formula II and the $R^2$ group represents a protecting group;

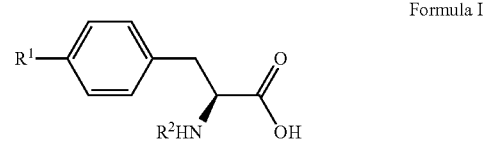

Formula I

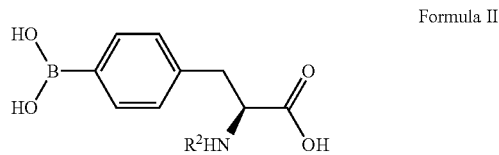

Formula II

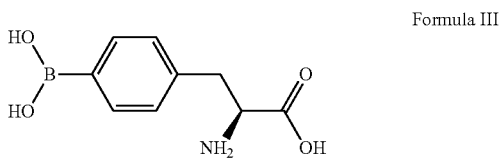

Formula III isolating the N-protected (S)-4-boronophenylalanine from the reaction mixture; and deprotecting the $R^2$ group of the N-protected (S)-4-boronophenylalanine to obtain L-BPA, wherein the L-BPA has a structure of Formula III.

Implementations of this aspect may include one or more of the following features.

More particularly, the $R^1$ group of N-protected (S)-4-halophenylalanine of Formula I is iodide or bromide, the $R^2$ group of N-protected (S)-4-halophenylalanine of Formula I and N-protected (S)-4-boronophenylalanine of Formula II is selected from the group consisting of: tert-butoxycarbonyl (t-Boc) group, trityl (Trt) group, 3,5-dimethoxyphenylisopropoxycarbonyl (Ddz) group, 2-(4-Biphenyl)isopropoxycarbonyl (Bpoc) group, and 2-nitrophenylsulfenyl (Nps) group, As a preferred one, the $R^2$ group is t-Boc. The boronating agent is trialkyl borate, the Grignard reagent includes alkylmagnesium chloride, alkylmagnesium bromide, arylmagnesium chloride or arylmagnesium bromide.

Further, the step of reacting N-protected (S)-4-halophenylalanine of Formula I, a boronating agent, Grignard reagent and bis(2-dimethylaminoethyl)ether to obtain a reaction mixture includes reacting N-protected (S)-4-halophenylalanine of Formula I, a boronating agent, Grignard reagent and bis(2-dimethylaminoethyl)ether at a temperature ranging from 0° C. to 60° C. to obtain the reaction mixture.

Further, the step of deprotecting the $R^2$ group of the N-protected (S)-4-boronophenylalanine to obtain L-BPA includes deprotecting the $R^2$ group of the N-protected (S)-4-boronophenylalanine at a temperature ranging from 30° C. to 60° C. to obtain L-BPA.

More particularly, the boronating agent has a $^{10}$B purity not less than 95%, the N-protected (S)-4-boronophenylalanine is N-protected (S)-4-($^{10}$B)boronophenylalanine of Formula IV and the L-BPA is L-$^{10}$BPA of Formula V.

Formula IV

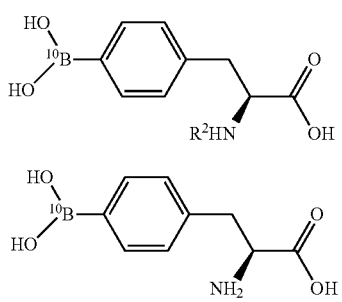

Formula V

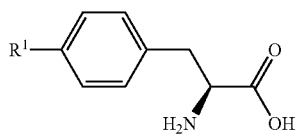

Further, the method for preparing L-BPA further includes a step of:

Formula VI

R¹—[benzene]—CH₂—CH(NH₂)—C(=O)OH protecting the amine terminal of (S)-4-halophenylatermilanine of Formula VI to obtain N-protected (S)-4-halophenylalanine of Formula I.

More particularly, the step of protecting the amine terminal of (S)-4-halophenylalanine of Formula VI to obtain N-protected (S)-4-halophenylalanine of Formula I includes:
- adding the (S)-4-halophenylalanine, 1,4-dioxane, water, sodium hydroxide and di-t-butyl dicarbonate into reaction vessel to perform the reaction;
- adjusting the pH value to less than 2 to crystallize the N-protected (S)-4-boronophenylalanine;
- adding a first extractive solvent so as to obtain N-protected (S)-4-boronophenylalanine.

Further, the method of preparing L-BPA further includes a step of reacting the boronic acid with sulfuric acid and butan-1-ol in a first organic solvent, to prepare the trialkyl borate.

More particularly, the step of isolating the N-protected (S)-4-boronophenylalanine from the reaction mixture includes:
- adding a second organic solvent and acid solution into the reaction mixture, adjusting pH value to less than 5, and extractive, to obtain organic phase;
- adding alkaline solution to said organic phase, adjusting the pH value to 7.1-14;
- adding a second extractive solvent so as to obtain the N-protected (S)-4-boronophenylalanine.

More particularly, the step of deprotecting the R² group of the N-protected (S)-4-boronophenylalanine to obtain L-BPA includes:
- adding the N-protected (S)-4-borono-L-phenylalanine, water, acid solution and a third organic solvent into a reaction vessel;
- adjusting the pH value to 6.15-6.25 so as to obtain L-BPA.

In another aspect of the present disclosure, the method for preparing L-BPA in accordance with the present disclosure includes steps of:
- reacting N-protected (S)-4-halophenylalanine of Formula I, a boronating agent and Grignard reagent to obtain a reaction mixture, wherein the reaction mixture includes N-protected (S)-4-boronophenylalanine of Formula II and the R² group represents a protecting group;

Formula I

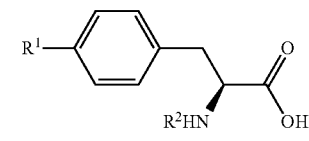

Formula II

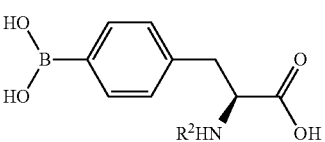

Formula III

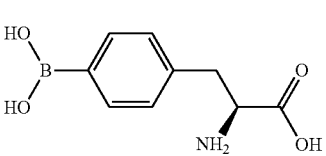

isolating the N-protected (S)-4-boronophenylalanine from the reaction mixture; and
deprotecting the R² group of the N-protected (S)-4-boronophenylalanine to obtain L-BPA, wherein the L-BPA has a structure of Formula III.

Implementations of this aspect may include one or more of the following features.

More particularly, the R¹ group of N-protected (S)-4-halophenylalanine of Formula I is iodide or bromide, the R² group of N-protected (S)-4-halophenylalanine of Formula I and N-protected (S)-4-boronophenylalanine of Formula II is selected from the group consisting of: tert-butoxycarbonyl (t-Boc) group, trityl (Trt) group, 3,5-dimethoxyphenylisopropoxycarbonyl (Ddz) group, 2-(4-Biphenyl)isopropoxycarbonyl (Bpoc) group, and 2-nitrophenylsulfenyl (Nps) group, As a preferred one, the R² group is t-Boc. The boronating agent is trialkyl borate, the Grignard reagent includes alkylmagnesium chloride, alkylmagnesium bromide, arylmagnesium chloride or arylmagnesium bromide.

Further, the step of reacting N-protected (S)-4-halophenylalanine of Formula I, a boronating agent and Grignard reagent to obtain a reaction mixture includes reacting N-protected (S)-4-halophenylalanine of Formula I, a boronating agent and Grignard reagent at a temperature ranging from 0° C. to 30° C. to obtain the reaction mixture.

More particularly, the boronating agent has a ¹⁰B purity not less than 95%, the N-protected (S)-4-boronophenylalanine is N-protected (S)-4-(¹⁰B)boronophenylalanine of Formula IV and the L-BPA is L-¹⁰BPA of Formula V.

Formula IV

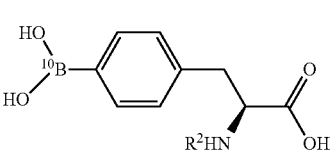

Formula V

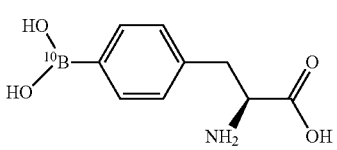

In yet another aspect of the present disclosure, the method for preparing L-BPA in accordance with the present disclosure includes steps of:

reacting N-protected (S)-4-halophenylalanine of Formula I, a boronating agent, Grignard reagent and bis(2-dimethylaminoethyl)ether to obtain a reaction mixture, wherein the reaction mixture includes N-protected (S)-4-boronophenylalanine of Formula II and the $R^2$ group represents a protecting group;

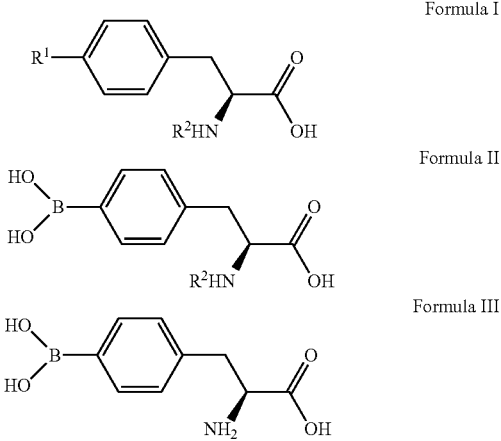

Formula I

Formula II

Formula III isolating the N-protected (S)-4-boronophenylalanine from the reaction mixture; and deprotecting the $R^2$ group of the N-protected (S)-4-boronophenylalanine to obtain L-BPA, wherein the L-BPA has a structure of Formula III;

wherein the $R^1$ group of N-protected (S)-4-halophenylalanine of Formula I is iodide or bromide, the $R^2$ group of N-protected (S)-4-halophenylalanine of Formula I and N-protected (S)-4-boronophenylalanine of Formula II is selected from the group consisting of: tert-butoxycarbonyl (t-Boc) group, trityl (Trt) group, 3,5-dimethoxyphenylisopropoxycarbonyl (Ddz) group, 2-(4-Biphenyl)isopropoxycarbonyl (Bpoc) group, and 2-nitrophenylsulfenyl (Nps) group, the boronating agent is trialkyl borate, the Grignard reagent includes alkylmagnesium chloride, alkylmagnesium bromide, arylmagnesium chloride or arylmagnesium bromide. As a preferred one, the $R^2$ group is t-Boc.

Implementations of this aspect may include one or more of the following features.

More particularly, the step of reacting N-protected (S)-4-halophenylalanine of Formula I, a boronating agent, Grignard reagent and bis(2-dimethylaminoethyl)ether to obtain a reaction mixture includes reacting N-protected (S)-4-halophenylalanine of Formula I, a boronating agent, Grignard reagent and bis(2-dimethylaminoethyl)ether at a temperature ranging from 0° C. to 60° C. to obtain the reaction mixture.

More particularly, the $R^1$ group of N-protected (S)-4-halophenylalanine of Formula I is iodide.

According to the present disclosure, the so-called "boronating agent" refers to any reagent that can replace the $R^1$ substituent of the N-protected (S)-4-halophenylalanine (i.e., the $R^1$ shown in Formula I) with boron-containing substituent (not limited todihydroxylboryl group), after the step of reacting N-protected (S)-4-halophenylalanine with boronating agent and Grignard reagent (whether bis(2-dimethylaminoethyl)ether is added or not).

According to the present disclosure, the boron element of the boronating agent can be the boron atom in any form, such as $^{11}B$, $^{10}B$ or a combination thereof (for Embodiment, the boron element in nature: the content of $^{10}B$ in the total of boron element is about 19.9%). As well known by one skilled in the art, the content of $^{10}B$ can also be other numbers of content, for Embodiment, the content of $^{10}B \geq 95\%$, in some embodiments of the present disclosure the content of $^{10}B$ is not limited.

Preferably, the boronating agent may include trialkyl borate, but as well known by one skilled in the art, it is not used herein for limiting the kinds of the boronating agent. The trialkyl borate may include: tributyl borate, triethyl borate, trimethyl borate, triisopropyl borate, tripropyl borate, tri-tert-butyl borate, or any suitable trialkyl borate. As a preferred one, the boronating agent is tributyl borate.

According to the present disclosure, the so-called "Grignard reagent" refers to any reagent that can replace the $R^1$ substituent of the N-protected(S)-4-halophenylalanine (i.e., the $R^1$ shown in Formula I) with boron-containing substituent (not limited todihydroxylboryl group), after the step of reacting N-protected (S)-4-halophenylalanine with boronating agent and Grignard reagent (whether bis(2-dimethylaminoethyl)ether is added or not). Preferably, the Grignard reagent is alkylmagnesium chloride or alkylmagnesium bromide or arylmagnesium chloride or arylmagnesium bromide. More preferably, the Grignard reagent is tert-butylmagnesium chloride or cyclohexylmagnesium chloride or tert-pentylmagnesium chloride. As a preferred one, the Grignard reagent is tert-butylmagnesium chloride (t-BuMgCl).

According to the present disclosure, the method for preparing L-BPA or L-10BPA may have a lot of advantages:

(1) Reacting N-protected (S)-4-halophenylalanine with boronating agent and Grignard reagent (whether bis(2-dimethylaminoethyl)ether is added or not), without pre-protecting the carboxylic acid group of N-protected (S)-4-halophenylalanine, then N-protected (S)-4-borono-L-phenylalanine is obtained. Therefore, during the latter part of preparation method, the step for deprotecting the carboxylic acid group is not necessary for the preparation methods, and the preparation method is significantly shortened;

(2) The boronating agent is directly used for taking part in the reaction, and the pre-preparation method for the preparation of boronating agent is simple and easy to achieve;

(3) It has the advantage that the preparation method is simple and easy, thus L-BPA prepared by the preparation method scan have the advantages of high chemical purity, high optical purity and excellent total yield, and so on. Therefore, a variety of time-saving, cost-saving and efficient preparation methods can be provided;

(4) One raw material for the preparation of boronating agent is boronic acid. This raw material has the advantages such as easy to get and price cheap, and so on, therefore the resulting boronating agent also has the advantages such as easy to get and price cheap, and so on.

According to the present disclosure, the use of tert-butylmagnesium chloride or cyclohexylmagnesium chloride or tert-pentylmagnesium chloride as the Grignard reagent in the method, may have the following advantages:

(1) It reacts at room temperature (0-30° C., the temperature can be lower, such as to −10° C., or the temperature can be higher, such as to 60° C.), so the reaction condition is easy to achieve, and the cost will be saved;

(2) It takes part in the reaction directly, and the preparation method is simple and easy, with a high yield.

According to the present disclosure, the use of tert-butoxycarbonyl group as the protecting group may have the following advantages:

(1) (S)—N-Boc-4-halophenylalanine (N-Boc-(S)-4-halophenylalanine) is solid, therefore it is easy to operate during the preparation method;

(2) One raw material for the preparation of (S)—N-Boc-4-halophenylalanine is di-t-butyl dicarbonate ($Boc_2O$). This raw material has the advantages such as easy to get and price cheap, and so on, therefore the resulting (S)—N-Boc-4-halophenylalanine also has the advantages such as easy to get and price cheap, and so on; and (3) After the deprotection of the tert-butoxycarbonyl group of (S)—N-Boc-4-boronophenylalanine, the tert-butoxycarbonyl group is broken down into carbon dioxide and tert-butanol, both of which are chemical substances of low danger, therefore the use of (S)—N-Boc-4-halophenylalanine for the preparation of L-BPA also has the advantages of safety and low danger.

Accordingly, the present disclosure avoids the complicated purification steps, and can successfully separate the N-protected(S)-4-borono-L-phenylalanine from the reaction mixture, through simple and easy preparation method scheme. Therefore, the method of the present disclosure can avoid the production of a large amount of waste solvents and silica gel, thus it also has the advantage of being friendly to the environment.

Accordingly, the present disclosure avoids the complicated purification steps, and can complete the step of deprotecting the protecting group of N-protected (S)-4-borono-L-phenylalanine, just through simple and easy preparation method scheme, and obtains L-BPA with high chemical purity and high optical purity from that. Therefore, the preparation method of the present disclosure can avoid the production of a large amount of waste solvents and silica gel, thus it also has the advantage of being friendly to the environment.

According to the present disclosure, the boronating agent may include trialkyl $^{10}B$ borate or any other suitable reagent with ≥98% $^{10}$boron purity. The trialkyl $^{10}B$ borate includes tributyl $^{10}B$ borate ($^{10}B(OBu)_3$), trimethyl $^{10}B$ borate ($^{10}B(OCH_3)_3$) or any other suitable trialkyl borate with above 98% $^{10}B$ purity, but as well known by one skilled in the art, it is not used herein for limiting the kinds of the boronating agent. More preferably, the boronating agent with ≥98% $^{10}B$ purity is a commercially available reagent, such as tributyl $^{10}B$ borate.

According to the present disclosure, the reaction solvents may include ether-type solvents, or any other suitable organic solvent, but are not limited to those. The selectable ether-type solvents of the present disclosure may include tetrahydrofuran, 2-methyltetrahydrofuran, diethyl ether, or any other suitable ether-type solvent.

According to the present disclosure, those organic solvents refer to organic materials in which the reactants are at least partially soluble, those organic solvent such as but not limited to: alkanes, ether-type solvents, or any other suitable organic solvent, such as toluene and acetone. The alkanes may include: hexanes, heptane, cyclohexane, pentane, or any other suitable alkane, but as well known by one skilled in the art, it is not used herein for limiting the kinds of the organic solvent. The ether-type solvents may include: methyl tert-butyl ether (MTBE), tetrahydrofuran (THF), diethyl ether, diethoxymethane, dibutyl ether, 2-methyltetrahydrofuran (2-MeTHF), or any other suitable organic solvent. Preferably, the first organic solvent is toluene, the second organic solvent is methyl tert-butyl ether, and the third organic solvent is acetone.

According to the present disclosure, the extractive solvent refers to any solvent that is materially insoluble in water or is only slightly soluble in water. The extractive solvent may include: isobutyl alcohol, toluene, butan-1-ol (n-butyl alcohol), isopropyl acetate, ethyl acetate, or any other suitable extractive solvent, but as well known by one skilled in the art, it is not used herein for limiting the kinds of the extractive solvent. Preferably, the first extractive solvent is ethyl acetate, and the second extractive solvent is butan-1-ol.

According to the present disclosure, the acid solution may include hydrochloric acid solution, or any other suitable acid solution, but as well known by one skilled in the art, it is not used herein for limiting the kinds of the acid solution. Preferably, the acid solution is 37% HCl.

According to the present disclosure, the alkaline solution may include sodium hydroxide solution, or any other suitable alkaline solution, but as well known by one skilled in the art, it is not used herein for limiting the kinds of the alkaline solution. Preferably, the alkaline solution is sodium hydroxide aqueous solution.

Further areas of applicability will become apparent from the description provided herein. It should be understood that the description and specific Embodiments are intended for purposes of illustration only and are not intended to limit the scope of the present disclosure.

DETAILED DESCRIPTION

As well known by one skilled in the art, the method for preparing L-BPA is basically the same as the method for preparing L-$^{10}$BPA. The difference lies in the use of boronating agent as the raw material, which has different contents of $^{10}$boron and $^{10}$boron. The boron content in the boronating agent as the raw material using for the preparation of L-BPA, can be the content of boron element existed in nature, which is about 19.9% $^{10}$boron and about 80.1% $^{11}$boron. The L-$^{10}$BPA with ≥95% $^{10}$boron content (i.e., element $^{10}$boron enriched L-BPA, normally called L-$^{10}$BPA) can also be used. Therefore, the method for preparing L-$^{10}$BPA disclosed by the embodiments of the present disclosure is also applicable to the method for preparing L-BPA. The Embodiment 1 of the present disclosure shows an Embodiment, in which boronating agent with ≥95% $^{10}$boron content, bis(2-dimethylaminoethyl)ether, and tert-butylmagnesium chloride as the Grignard reagent are used as the raw material for the preparation of L-$^{10}$BPA. The one with another ratio of $^{10}$boron content can also be prepared by the same preparation method; the Embodiment 2 of the present disclosure discloses the steps of preparing (S)—N-Boc-4-borono-L-phenylalanine from (S)—N-Boc-4-iodophenylalanine, and the steps of deprotecting the amine terminal of (S)—N-Boc-4-borono-L-phenylalanine to prepare L-BPA, using boronating agent with common $^{10}$boron content, bis(2-dimethylaminoethyl)ether and tert-butylmagnesium chloride as the Grignard reagent as the raw material; the Embodiment 3 of the present disclosure discloses the steps of preparing (S)—N-Boc-4-borono-L-phenylalanine from (S)—N-Boc-4-iodophenylalanine, using boronating agent with common $^{10}$boron content, bis(2-dimethylaminoethyl)ether and tert-butylmagnesium chloride as the Grignard reagent as the raw material; the Embodiment 4 of the present disclosure discloses the steps of preparing (S)—N-Boc-4-borono-L-phenylalanine from (S)—N-Boc-4-iodophenylalanine, using boronating agent with common $^{10}$boron content, bis(2-dimethylaminoethyl)ether and cyclohexylmagnesium chloride as the Grignard reagent as the raw material; the Embodiment 5 of the present disclosure discloses the steps of preparing (S)—N-Boc-4-borono-L-phenylalanine from (S)—N-Boc-4-iodophenylalanine, using boronating agent with common $^{10}$boron content, bis(2-dimethylaminoethyl)ether and tert-pentylmagnesium chloride as the Grignard reagent as the raw material; the Embodiments 6-7 of the present disclosure discloses the steps of preparing (S)—N-Boc-4-borono-L-phenylalanine from (S)—N-Boc-4-iodophenylalanine, using boronating agent with common $^{10}$boron content and tert-butylmagnesium chloride as the Grignard reagent as the raw material, without the addition of bis(2-dimethylaminoethyl)ether.

In the Embodiments 2-7 of the present disclosure, the prior steps of the preparation of L-BPA are basically the same as those described in Embodiment 1, except the difference of $^{10}$boron content, therefore those steps will not be repeated in detail in those Embodiments. In the Embodiments 3-7 of the present disclosure, the steps of amine terminal deprotection of the preparation of L-BPA are basically the same as those described in Embodiment 2, therefore those steps will not be repeated in detail in those Embodiments.

In the Embodiments below, (S)—N-Boc-4-iodophenylalanine is used as the preferred Embodiment of N-protected (S)-4-halophenylalanine, and (S)—N-Boc-4-iodophenylalanine is used to prepare L-BPA or L-$^{10}$BPA, to explain that the embodiments of the present disclosure overcome the technical defects of the prior art. Through the contents of the present specification, one skilled in the art can easily realize the advantages and effects achieved by the present disclosure, and give out various modifications and changes without departing the spirit of the present disclosure, to implement or apply the contents of the present disclosure. It is also known that the Embodiments cited herein are not used to limit the scope of the claims of the present disclosure.

Embodiment 1

Before preparing (S)—N-Boc-4-boronophenylalanine from (S)—N-Boc-4-iodophenylalanine, it is necessary to disclose the method for preparing (S)—N-Boc-4-iodophenylalanine from (S)-4-iodophenylalanine as the raw material, and the method for preparing tributyl $^{10}$B borate from $^{10}$Boronic acid.

1. Preparing (S)—N-Boc-4-iodophenylalanine from (S)-4-iodophenylalanine

With reference to the following Reaction Formula I, it is the chemical reaction formula of reaction between (S)-4-iodophenylalanine and sodium hydroxide (NaOH) and di-t-butyl dicarbonate (Boc$_2$O) in the solvents of 1,4-dioxane and water (H$_2$O) to prepare (S)—N-Boc-4-iodophenylalanine.

Reaction Formula I

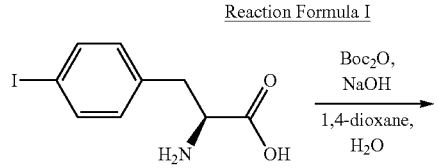

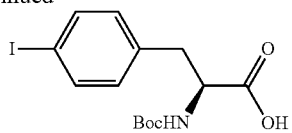

During the preparation process, two reaction vessels were selected to perform the reaction.

The specific operation method is as follows:

A reaction was set up, using 3 L three-necked flask. (S)-4-iodo-L-phenylalanine (200.00 g, 687.10 mmol, 1.00 eq), 1,4-dioxane (1.00 L) and water (1.00 L) were separately added into the reaction system, followed by sodium hydroxide (68.71 g, 1.72 mol, 2.50 eq), then the solution gradually became clear, and the temperature rose slightly to 19° C. When the system was cooled down to 0-10° C., di-t-butyl dicarbonate (254.93 g, 1.17 mol, 268.35 mL, 1.70 eq) was added into the reaction system, then the temperature of the reaction system naturally rose to 10~30° C. After addition, the reaction system was stirred at room temperature (about 30° C.) for eight hours. High performance liquid chromatography (HPLC) was used to detect the reaction, until the reaction of the raw material was completed. Then the system temperature was controlled below 40° C., and 1,4-dioxane was concentrated. The reaction mixture was quenched with 100 mL water after the temperature of reaction system was cooled down to room temperature (about 25° C.), and the pH was adjusted to 1.8-2 by hydrochloric acid (2M (i.e., molarity (M))). The result reaction mixture was extracted three times with ethyl acetate (2 L). The obtained organic phases were combined, and washed twice with saturated salt water (1 L), dried by sodium sulfate (200 g) and rotary evaporating, to give a crude product as a yellowish solid. The crude product was subsequently dried in an oven (40-45° C.), to give a white solid (S)—N-Boc-4-iodo-L-phenylalanine (250.00 g, 626.28 mmol, analyzed by HPLC, 93.00% yield, 98% purity).

The analysis results of the resulting (S)—N-Boc-4-iodo-L-phenylalanine by $^1$Hydrogen nuclear magnetic resonance spectroscopy ($^1$HNMR) were described as follows:

$^1$HNMR: (400 MHz DMSO-d$_6$)

δ 7.49 (d, J=7.8 Hz, 2H), 6.88 (d, J=7.8 Hz, 2H), 5.80 (d, J=5.9 Hz, 1H), 3.68 (d, J=5.5 Hz, 1H), 3.00-2.90 (m, 1H), 2.87-2.75 (m, 1H), 1.35-1.15 (m, 9H).

2. Preparation of Tributyl $^{10}$B Borate from $^{10}$Boronic Acid

With reference to the following Reaction Formula II, it is the chemical reaction formula of reaction between $^{10}$Boronic acid and sulfuric acid (H$_2$SO$_4$) in the solvents of butan-1-ol and toluene to prepare tributyl $^{10}$B borate ($^{10}$B(OBu)$_3$).

Reaction Formula II

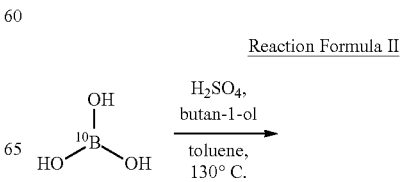

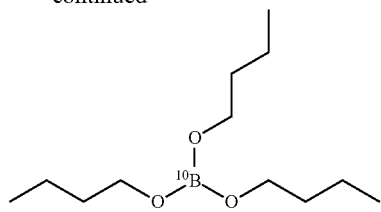

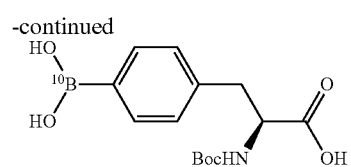

During the preparation process, two reaction vessels were selected to perform the reaction.

The specific operation method is as follows:

The reaction device R1 was set up, using 3 L three-necked flask, equipped with a water segregator. $^{10}$Boronic acid (150.00 g, 2.46 mol, 1.00 eq), butan-1-ol (1.00 L) was added into the reaction R1 and stirred, and most of boronic acid cannot be dissolved. Then toluene (1.00 L) was added into the reaction R1 and stirred at room temperature (about 25° C.). Concentrated sulfuric acid (4.82 g, 49.16 mmol, 2.62 mL, 0.02 eq) was dropwise added into the reaction at room temperature (about 25° C.), a large number of solids were still remained undissolved. After that, the temperature of reaction system was risen to 130° C., and stirred for 3.5 hours while keeping segregating the water out. The water generated in the water segregator (about 140 g) was separated, all of solids were dissolved, and the solution was changed from colorless to brown. TLC analysis (DCM: MeOH=5:1, Rf=0.43, coloured by bromocresol green) of the mixture showed the completion of the reaction. Most of the toluene was distilled off under normal pressure. After that, the system temperature was cooled down to 20~30° C. The reaction liquids from two reactions were combined, and the device was changed for distillation. With an outer temperature of the oil bath of 108-110° C., the butan-1-ol was distilled off by water pump vacuum distillation, at 45° C. measured by the Kelvin thermometer, and the residual butanol was distilled off by oil pump vacuum distillation. Raise the temperature to 118-120° C., the product began to be distilled off by oil pump vacuum distillation at 55° C. measured by the Kelvin thermometer, and continue to raise the temperature to 135-140° C. until the product was distilled off. The resulting product was tributyl $^{10}$B borate as a colorless liquid (830.00 g, 3.62 mol, 73.58% yield).

The analysis results of the resulting tributyl $^{10}$B borate by $^1$HNMR were described as follows:

$^1$H NMR: (400 MHz CDCl$_3$)

δ3.82-3.68 (m, 6H), 1.57-1.42 (m, 6H), 1.34 (qd, J=7.4, 14.9 Hz, 6H), 0.95-0.80 (m, 9H).

3. Preparation of (S)—N-Boc-4-$^{10}$borono-L-phenylalanine from (S)—N-Boc-4-iodophenylalanine With reference to the following Reaction Formula III, it is the chemical reaction formula of reaction between (S)—N—Boc-4-iodophenylalanine, tributyl $^{10}$B borate, tert-butylmagnesium chloride (t-BuMgCl) and bis(2-dimethylaminoethyl)ether (BDMAEE) to prepare (S)—N-Boc-4-($^{10}$B) borono-L-phenylalanine.

Reaction Formula III

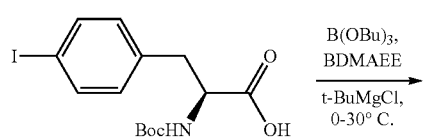

A reaction was set up, using 3 L three-necked flask. Tributyl $^{10}$B borate (187.60 g, 817.98 mmol, 3.20 eq), sodium hydride (20.45 g, 511.24 mmol, 60% purity, 2.00 eq) was added all at once into the reaction system, at that time, the reaction liquid was a suspension, which was stirred for 5 minutes at room temperature (about 22° C.). Then bis(2-dimethylaminoethyl)ether (327.73 g, 2.04 mol, 8.00 eq) and N-Boc-4-iodo-L-phenylalanine (100.00 g, 255.62 mmol, 1.00 eq) was added into the reaction system at room temperature (about 22° C.), and a large number of solids were not dissolved. After that, the temperature of reaction system was cooled down to 0-5° C., and tert-butylmagnesium chloride (1.7 M, 1.20 L, 2.04 mol, 8.00 eq) was dropwise added into the reaction. Mainwhile, the temperature was controlled to be 0-10° C., and the dropping time was about 1.5 hours. After the material addition was completed, the temperature of reaction system naturally rose to room temperature (20~30° C.), continue stirred under this temperature for 12 hours. High performance liquid chromatography (HPLC) was used for detection, and the remaining of raw material was about 9.00%. When the temperature of reaction system was cooled down to −5-0° C., the reaction was quenched by dropwise addition of 500 mL water. Methyl tert-butyl ether (500 mL) was added into the reaction system at 0-5° C., and the pH was adjusted to 2.9-3.1 (by pH meter) by 37% HCl (about 500 mL). During the pH adjusting process, the system temperature was controlled to be 0-15° C. The resulting aqueous phase from liquid separating was extracted once with methyl tert-butyl ether (500 mL), the resulting organic phases were combined, to give about 1.1 L organic phases. Sodium hydroxide aqueous solution (1M, 400 mL) was dropwise added into the resulting organic phase slowly. During the dropwise addition process, the system temperature was controlled to be 0-15° C. After the dropwise addition was completed, the pH value of the system was about 10, then adjusted the pH value to 12.1-12.6 (determined by pH meter) by sodium hydroxide aqueous solution (4M). The resulting aqueous phase 1 was obtained by separating the mixture, the extracted once with butan-1-ol (500 ml) to give the aqueous phase 2. The resulting aqueous phases of the reaction in the two reaction vessels were combined, and then the pH value of the resulting aqueous phases was adjusted to 2.9-3.1 by 37% HCl. After stirred for about 40 minutes, a large amount of solids were precipitated. The white solid was collected by filtration and drip washed once with methylene chloride (50 mL). At 25° C., the precipitated solid was slurried with methylene chloride (150 mL), and stirred for 10 minutes. The resulting white solid was filtrated to give (S)—N-Boc-4-($^{10}$B) borono-L-phenylalanine (75.00 g, 240.82 mmol, analyzed by HPLC, 47.11% yield, 99% purity).

The analysis results of the resulting (S)—N-Boc-4-($^{10}$B) borono-L-phenylalanine by $^1$HNMR were described as follows:

$^1$HNMR: (400 MHz DMSO-d$_6$)

δ2.55 (br. s., 1H), 7.91 (s, 2H), 7.66 (d, J=7.5 Hz, 2H), 7.17 (d, J=7.5 Hz, 2H), 4.08-4.01 (m, 1H), 3.61-3.53 (m, 1H), 2.98 (dd, J=4.2, 13.9 Hz, 1H), 2.79 (dd, J=10.4, 13.5 Hz, 1H), 1.79-1.67 (m, 1H), 1.35-1.17 (m, 9H).

4. Preparing L-$^{10}$BPA from (S)—N-Boc-4-borono-L-phenylalanine

With reference to the following Reaction Formula IV, it is the chemical reaction formula of deprotecting the amine terminal of (S)—N-Boc-4-($^{10}$B)borono-L-phenylalanine to prepare L-$^{10}$BPA.

Reaction Formula IV

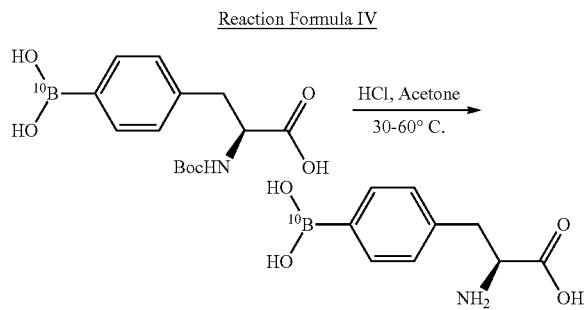

The specific operation method is as follows:

A reaction was set up, using 1 L three-necked flask. (S)—N-Boc-4-($^{10}$B) borono-L-phenylalanine (67.00 g, 217.31 mmol, 1.00 eq), water (23.75 mL) and acetone (420.00 mL) was added into the reaction system and stirred at room temperature (20-30° C.). Then concentrated hydrochloric acid (23.93 g, 656.28 mmol, 23.46 mL, 3.02 eq) was dropwise added into the reaction system. After the dropwise addition was completed, the temperature of reaction system was risen to 55-60° C., and the reaction system was stirred for 4.5 hours. HPLC analysis of the mixture showed the completion of the reaction. The acetone in the reaction system was concentrated with the temperature below 40° C. After the concentration, the system was cooled down to below 15° C., and the pH value of the system was adjusted to about 1.5 (detected by pH meter) by sodium hydroxide solution (4M). After stirring for 40 minutes, the pH value of the system was adjusted to 6.15~6.25 by continuously adding sodium hydroxide solution (4M), and a large amount of white solids were precipitated. The white solid was collected by filtration and drip washed with acetone (200 mL). The white solid L-$^{10}$BPA was obtained (36.00 g, 171.17 mmol, analyzed by HPLC, 78.77% yield, 99% purity).

The analysis results of the resulting L-$^{10}$BPA by $^1$HNMR were described as follows:

$^1$H NMR: (400 MHz D$_2$O, CF$_3$COOH)
δ7.44 (d, J=7.9 Hz, 1H), 7.03 (d, J=7.9 Hz, 1H), 4.06 (dd, J=5.7, 7.5 Hz, 1H), 3.11-3.01 (m, 1H), 2.98-2.87 (m, 1H).

Embodiment 2

1. Preparing (S)—N-Boc-4-borono-L-phenylalanine from (S)—N-Boc-4-iodophenylalanine With reference to Reaction Formula III', it is the chemical reaction formula of reaction between (S)—N-Boc-4-iodophenylalanine, tributyl borate, tert-butylmagnesium chloride (t-BuMgCl) and bis(2-dimethylaminoethyl)ether (BDMAEE) to prepare (S)—N-Boc-4-borono-L-phenylalanine.

Reaction Formula III'

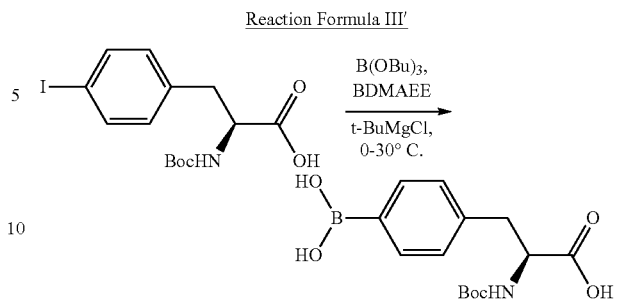

The specific operation method is as follows:

A reaction device was set up, using 100 mL three-necked flask. At the temperature of 20~30° C., tributyl borate (5.65 g, 24.54 mmol, 3.20 eq), sodium hydride (613.50 mg, 15.34 mmol, 2.00 eq), bis(2-dimethylaminoethyl)ether (9.83 g, 61.35 mol, 8.00 eq) and (S)—N-Boc-4-iodophenylalanine (3.00 g, 7.67 mmol, 1.00 eq) was added into the 100 mL flask. Under nitrogen atmosphere, the temperature of reaction system was cooled down to 0° C., tert-butylmagnesium chloride (1.7 M in tetrahydrofuran, 36 mL, 8.00 eq) was dropwise added into the reaction, the dropping time was about 30 minutes, and the temperature was controlled to be 0° C.-10° C. Then the reaction system was stirred for 16 hours at 20~30° C. Detected by HPLC, the reaction of the raw material was not completed, and the remaining of raw material was about 13%. At the temperature of 0° C., 1.5 mL water was dropwise added into the reaction for quenching. After the quenching was completed, the stirring continued for 10 minutes. Methyl tert-butyl ether (15 mL) was added into the reaction at 0° C., and the pH value was adjusted to 3 (detected by pH meter) by 37% HCl (about 15 mL). During the pH adjusting process, the temperature was controlled to be 0° C.-15° C. The resulting aqueous phase from liquid separating was extracted once with methyl tert-butyl ether (15 mL). The two organic phases were combined. NaOH solution (1M, 17 mL) was dropwise added into the resulting organic phase, and the pH value was adjusted to 12.1-12.6. During this process, the temperature was controlled to be 0° C.-15° C. The liquids were separated, and the resulting aqueous phase was extracted once with butan-1-ol (15 ml), to remove most of the impurities by extraction. The resulting aqueous phase from liquid separating was adjusted by 37% HCl to pH=3, stirred for about 30 minutes, and large amount of white solids were precipitated. The white solid was collected by filtration and drip washed once with methylene chloride (15 mL). The precipitated solid was slurried with 8 mL methylene chloride, and stirred for 10 minutes at 25° C. The white solid(S)—N-Boc-4-borono-L-phenylalanine was obtained by filtration (1.80 g, 5.82 mmol, analyzed by HPLC, 75.92% yield, 100% purity).

The analysis results of the resulting(S)—N-Boc-4-borono-L-phenylalanine by $^1$HNMR were described as follows:

$^1$H NMR: (400 MHz DMSO-d$_6$)
δ=7.95 (s, 2H), 7.69 (d, J=7.7 Hz, 2H), 7.19 (d, J=7.7 Hz, 2H), 7.07 (d, J=8.4 Hz, 1H), 4.14-4.04 (m, 1H), 3.00 (br dd, J=4.4, 13.7 Hz, 1H), 2.82 (br dd, J=10.5, 13.8 Hz, 1H), 1.32 (s, 9H).

2. Preparing L-BPA from (S)—N-Boc-4-borono-L-phenylalanine

With reference to the following Reaction Formula IV', it is the chemical reaction formula of deprotecting the amine terminal of (S)—N-Boc-4-borono-L-phenylalanine to prepare L-BPA.

Reaction Formula IV'

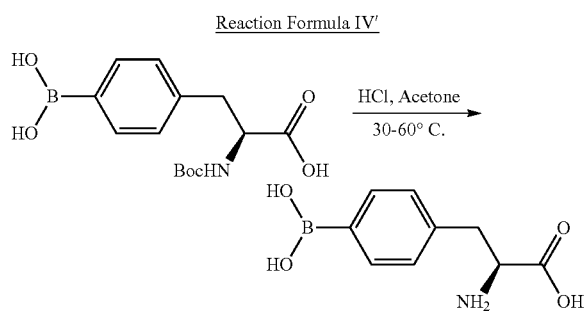

The specific operation method is as follows:

A reaction device was set up, using 100 mL three-necked flask. At the temperature of 20~30° C., (S)—N-Boc-4-borono-L-phenylalanine (1.80 g, 5.82 mmol, 1.00 eq), water (0.63 mL) and acetone (11.30 mL) were separately added into the flask. Then HCl (17.46 mmol, 1.46 mL, 3.00 eq) was dropwise added into the reaction. After the dropwise addition was completed, the temperature of reaction was risen to 60° C., and the reaction was stirred for 4 hours. HPLC detection indicated that the reaction was already completed. The reaction liquid was concentrated under reduced pressure at 40° C. with most of acetone was rotary evaporated. The temperature was cooled down to 0~15° C., and the pH value was adjusted to 1.5 by NaOH solution (4M), and the solids started precipitated. The pH value was adjusted continuously to 6.2, and a large amount of white solids were precipitated, stirred for 15 minutes. The white solid was collected by filtration and drip washed with acetone (6 mL), then transferred and dried by rotary evaporating. The resulting white solid L-BPA was obtained (0.85 g, 4.07 mmol, analyzed by HPLC, 70.18% yield, 98% purity).

The analysis results of the resulting L-BPA by $^1$HNMR were described as follows:

$^1$H NMR: (400 MHz D$_2$O)

δ=7.62 (d, J=7.5 Hz, 2H), 7.22 (d, J=7.9 Hz, 2H), 3.86 (dd, J=5.5, 7.5 Hz, 1H), 3.20-3.13 (m, 1H), 3.05-2.97 (m, 1H).

Embodiment 3

Preparing (S)—N-Boc-4-borono-L-phenylalanine from (S)—N-Boc-4-iodophenylalanine

With reference to Reaction Formula III' once more, the specific operation method is as follows:

A reaction device was set up, using 1 L three-necked flask. At 20~30° C., tributyl borate (56.48 g, 245.40 mmol, 3.20 eq), sodium hydride (6.13 g, 153.37 mmol, 2.00 eq), bis(2-dimethylaminoethyl)ether (98.32 g, 613.50 mol, 8.00 eq) and (S)—N-Boc-4-iodophenylalanine (30.00 g, 76.69 mmol, 1.00 eq) was added into the 1 L flask. Under nitrogen atmosphere, the temperature of reaction system was cooled down to 0° C., tert-butylmagnesium chloride (1.7 M in tetrahydrofuran, 360 mL, 8.00 eq) was dropwise added into the reaction, the dropping time was about 1 hour, and the temperature was controlled to be 0° C.-10° C. Then the reaction system was stirred for 16 hours at 20~30° C. Detected by HPLC, the reaction of the raw material was not completed, and the remaining of raw material was about 8%. 15 mL water was dropwise added into the reaction for quenching at the temperature of 0° C. After the quenching completely, the stirring continued for 10 minutes. Methyl tert-butyl ether (150 mL) was added into the reaction at 0° C., and the pH was adjusted to 3 (detected by pH meter) by 37% HCl (about 160 mL). During the pH adjusting process, the temperature was controlled to be 0° C.-15° C. The resulting aqueous phase from liquid separating was extracted once with methyl tert-butyl ether (150 mL), and the two organic phases were combined. After that, NaOH solution (1M, 190 mL) was dropwise added into the resulting organic phase, and the pH value was adjusted to 12.1-12.6. During this process, the temperature was controlled to be 0° C.-15° C. The resulting aqueous phase, separated from the liquids, was extracted once with butan-1-ol (150 ml), to remove most of the impurities by extraction. The resulting aqueous phase from liquid separating was adjusted by 37% HCl to pH=3, and stirred for 30 minutes, and a large amount of white solids were precipitated. The white solid was collected by filtration and drip washed once with methylene chloride (150 mL). Then, the precipitated solid was slurried with 80 mL methylene chloride, and stirred for 10 minutes at 25° C. The resulting white solid (S)—N-Boc-4-borono-L-phenylalanine was obtained by filtration (15.00 g, 48.52 mmol, analyzed by HPLC, 63.27% yield, 100% purity).

The analysis results of the resulting (S)—N-Boc-4-borono-L-phenylalanine by $^1$HNMR were described as follows:

$^1$H NMR: (400 MHz DMSO-d$_6$)

δ=7.97 (s, 2H), 7.68 (d, J=7.9 Hz, 2H), 7.23-7.16 (m, 2H), 7.08 (d, J=8.4 Hz, 1H), 4.12-4.04 (m, 1H), 3.00 (dd, J=4.4, 13.7 Hz, 1H), 2.81 (dd, J=10.4, 13.7 Hz, 1H), 1.34-1.23 (m, 9H).

Embodiment 4

Preparing (S)—N-Boc-4-borono-L-phenylalanine from (S)—N-Boc-4-iodophenylalanine

With reference to the following Reaction Formula V, it is the chemical reaction formula of reaction between (S)—N-Boc-4-iodophenylalanine, tributyl borate, cyclohexylmagnesium chloride (c-HexMgCl) and bis(2-dimethylaminoethyl)ether (BDMAEE) to prepare (S)—N-Boc-4-borono-L-phenylalanine.

Reaction Formula V

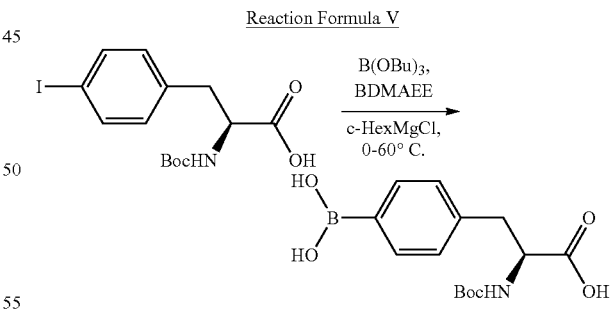

The specific operation method is as follows:

A reaction device was set up, using 100 mL three-necked flask. At 20~30° C., tributyl borate (2.82 g, 12.27 mmol, 3.20 eq), bis(2-dimethylaminoethyl)ether (4.92 g, 30.67 mol, 8.00 eq), (S)—N-Boc-4-iodo-L-phenylalanine (1.50 g, 3.83 mmol, 1.00 eq) was added into the 100 mL flask. Under nitrogen atmosphere, the temperature of reaction system was cooled down to 0° C., cyclohexylmagnesium chloride (2 M in diethyl ether, 15 mL, 8.00 eq) was dropwise added into the reaction, the dropping time was about 20 minutes, and the temperature was controlled to be 0° C.-10° C. After addition, the reaction system was stirred for 24 hours at 20~30° C., then stirred for 24 hours at 60±5° C. Detected by HPLC, the reaction of the raw material was not completed, and the remaining of raw material was about 83%. 0.75 mL water was dropwise added into the reaction for quenching at 0° C. After the quenching was completed, the stirring continued for 10 minutes. After that, methyl tert-butyl ether (7.5 mL) was added into the reaction at 0° C., and the pH value was adjusted to 3 (detected by pH meter) by 37% HCl (about 7.5 mL). Heat was released. During the pH adjusting process, the temperature was controlled to be 0° C.-15° C. The resulting aqueous phase from liquid separating was extracted once with methyl tert-butyl ether (7.5 mL). The two organic phases were combined. NaOH solution (1M, 8.5 mL) was dropwise added into the resulting organic phase, and the pH was adjusted to 12.1-12.6. Heat was released. During this process, the temperature was controlled to be 0° C.-15° C. The liquids were separated, and the resulting aqueous phase was extracted once with butan-1-ol (7.5 ml), to remove most of the impurities by extraction. The resulting aqueous phase from liquid separating was adjusted by 37% HCl to pH=3, and stirred for about 30 minutes. The white solid was precipitated, collected by filtration, and drip washed once with methylene chloride (7.5 mL). The precipitated solid was slurried with 4 mL methylene chloride, and stirred for 10 minutes at 25° C. Finally, the white solid (S)—N-Boc-4-borono-L-phenylalanine was obtained by filtration (0.2 g, analyzed by HPLC, 14.83% yield, 99% purity).

The analysis results of the resulting (S)—N-Boc-4-borono-L-phenylalanine by $^1$HNMR were described as follows:

$^1$H NMR: (400 MHz DMSO-$d_6$)

δ=7.96 (s, 2H), 7.67 (d, J=7.9 Hz, 2H), 7.21 (d, J=7.7 Hz, 2H), 7.09 (d, J=8.4 Hz, 1H), 4.12-4.04 (m, 1H), 3.00 (br dd, J=4.4, 13.7 Hz, 1H), 2.83 (dd, J=10.4, 13.7 Hz, 1H), 1.33-1.21 (m, 9H).

Embodiment 5

Preparing (S)—N-Boc-4-borono-L-phenylalanine from (S)—N-Boc-4-iodophenylalanine

With reference to the following Reaction Formula VI, it is the chemical reaction formula of reaction between (S)—N-Boc-4-iodophenylalanine, tributyl borate, tert-pentylmagnesium chloride (t-PenMgCl) and bis(2-dimethylaminoethyl)ether (BDMAEE) to prepare (S)—N-Boc-4-borono-L-phenylalanine.

Reaction Formula VI

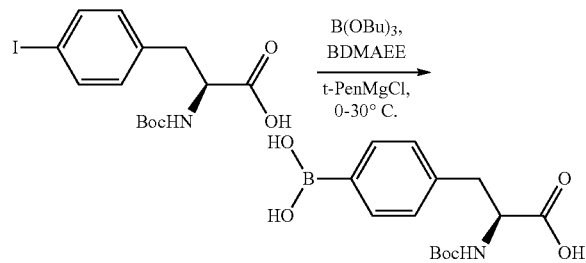

The specific operation method is as follows:

A reaction device was set up, using 100 mL three-necked flask. At 20~30° C., tributyl borate (2.82 g, 12.27 mmol, 3.20 eq), bis(2-dimethylaminoethyl)ether (4.92 g, 30.67 mol, 8.00 eq), (S)—N-Boc-4-iodo-L-phenylalanine (1.50 g, 3.83 mmol, 1.00 eq) was added in batches into the 100 mL flask. Under nitrogen atmosphere, the temperature of reaction system was cooled down to 0° C., tert-pentylmagnesium chloride (1.0 M in 2-MeTHF, 31 mL, 8.00 eq) was dropwise added into the reaction, the dropping time was about 20 minutes, and the temperature was controlled to be 0° C.-10° C. After addition, the reaction system was stirred for 24 hours at 20~30° C., and stirred for 24 hours at 60±5° C. Then detected by HPLC, the reaction of the raw material was not completed, and the remaining of raw material was about 47%. 0.75 mL water was dropwise added into the reaction for quenching at 0° C. After the quenching was completed, the stirring continued for 10 minutes. Methyl tert-butyl ether (7.5 mL) was added into the reaction at 0° C., and the pH value was adjusted to 3 (detected by pH meter) by 37% HCl (about 7.5 mL). Heat was released during the pH adjusting process, and the temperature was controlled to be 0° C.-15° C. The resulting aqueous phase from liquid separating was extracted once with methyl tert-butyl ether (7.5 mL). The two organic phases were combined. NaOH solution (1M, 8.5 mL) was dropwise added into the resulting organic phase, and the pH value was adjusted to 12.1-12.6. Heat was released during this process, and the temperature was controlled to be 0° C.-15° C. The resulting aqueous phase, separated from the liquids, was extracted once with butan-1-ol (7.5 ml), to remove most of the impurities by extraction. The resulting aqueous phase from liquid separating was adjusted by 37% HCl to pH=3, and stirred for about 30 minutes. The white solid were precipitated, collected by filtration and drip washed once with methylene chloride (7.5 mL). The precipitated solid was slurried with 4 mL methylene chloride, and stirred for 10 minutes at 25° C. The white solid (S)—N-Boc-4-borono-L-phenylalanine was obtained by filtration (0.5 g, analyzed by HPLC, 46.25% yield, 98% purity).

The analysis results of the resulting (S)—N-Boc-4-borono-L-phenylalanine by $^1$HNMR were described as follows:

$^1$H NMR: (400 MHz DMSO-$d_6$)

δ=7.98 (s, 2H), 7.70 (d, J=7.9 Hz, 2H), 7.23 (d, J=7.7 Hz, 2H), 7.10 (d, J=8.4 Hz, 1H), 4.13-4.04 (m, 1H), 3.00 (br dd, J=4.4, 13.7 Hz, 1H), 2.84 (dd, J=10.4, 13.7 Hz, 1H), 1.33-1.24 (m, 9H).

Embodiment 6

Preparing (S)—N-Boc-4-borono-L-phenylalanine from (S)—N-Boc-4-iodophenylalanine

With reference to the following Reaction Formula VII, it is the chemical reaction formula of reaction between (S)—N-Boc-4-iodophenylalanine, tributyl borate and tert-butylmagnesium chloride (t-BuMgCl) to prepare (S)—N-Boc-4-borono-L-phenylalanine.

Reaction Formula VII

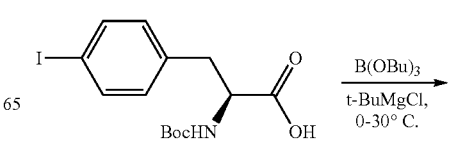

-continued

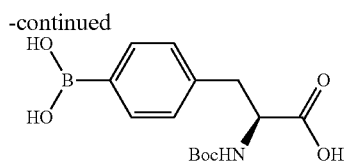

The specific operation method is as follows:

A reaction device was set up, using 250 mL three-necked flask. At 20~30° C., tributyl borate (17.65 g, 76.68 mmol, 3.00 eq), sodium hydride (1.02 g, 25.56 mmol, 1.00 eq), (S)—N-Boc-4-iodo-L-phenylalanine (10.00 g, 25.56 mmol, 1.00 eq) was added into the flask. Under nitrogen atmosphere, the temperature of reaction system was cooled down to 0° C., tert-butylmagnesium chloride (1.7 M in THF, 120 mL, 8.00 eq) was dropwise added into the reaction slowly, the dropping time was about 30 minutes, and the temperature was controlled to be 0° C.-10° C. Then the reaction system was stirred for 20 hours at 20~30° C. Detected by HPLC, the reaction of the raw material was almost completed, and the remaining of raw material was only about 0.7%. 5 mL water was dropwise added into the reaction for quenching at 0° C. After the quenching was completed, the stirring continued for 10 minutes. Methyl tert-butyl ether (50 mL) was added into the reaction at 0° C., and the pH value was adjusted to 3 (detected by pH meter) by 37% HCl (about 50 mL). Heat was released during the pH adjusting process, and the temperature was controlled to be 0° C.-15° C. The resulting aqueous phase from liquid separating was extracted once with methyl tert-butyl ether (50 mL). The two organic phases were combined. NaOH solution (1M, 55 mL) was dropwise added into the resulting organic phase, and the pH value was adjusted to 12.1-12.6. Heat was released during this process, and the temperature was controlled to be 0° C.-15° C. The resulting aqueous phase, separated from the liquids, was extracted once with butan-1-ol (50 mL), to remove most of the impurities by extraction. Then adjusted by 37% HCl to pH=3, and stirred for about 30 minutes. The white solid was precipitated, collected by filtration and drip washed once with methylene chloride (50 mL). After that, the precipitated solid was slurried with 25 mL methylene chloride, and stirred for 10 minutes at 25° C. Finally, The white solid (S)—N-Boc-4-borono-L-phenylalanine was obtained by filtration (6.8 g, analyzed by HPLC, 83.15% yield, 98% purity).

Embodiment 7

With reference to Reaction Formula VII once more, the specific operation method is as follows:

A reaction device was set up, using 250 mL three-necked flask. At 20~30° C., tributyl borate (8.82 g, 38.34 mmol, 3.00 eq), sodium hydride (511.25 mg, 12.78 mmol, 1.00 eq), (S)—N-Boc-4-iodo-L-phenylalanine (5.00 g, 12.78 mmol, 1.00 eq) was added into the 250 mL flask. Under nitrogen atmosphere, the temperature of reaction system was cooled down to 0° C., tert-butylmagnesium chloride (1.7 M in THF, 60 mL, 8.00 eq) was dropwise added into the reaction, the dropping time was about 30 minutes, and the temperature was controlled to be 0° C.-10° C. Then the reaction system was stirred for 22 hours at 20~30° C. Detected by HPLC, the reaction of the raw material was completed. 2.5 mL water was dropwise added into the reaction for quenching at 0° C. After the quenching was completed, the stirring continued for 10 minutes. Methyl tert-butyl ether (25 mL) was added into the reaction at 0° C., and the pH value was adjusted to 3 (detected by pH meter) by 37% HCl (about 25 mL). Heat was released during the pH adjusting process, and the temperature was controlled to be 0° C.-15° C. The resulting aqueous phase from liquid separating was extracted once with methyl tert-butyl ether (25 mL). The two organic phases were combined. NaOH solution (1M, 30 mL) was dropwise added into the resulting organic phase, and the pH value was adjusted to 12.1-12.6. Heat was released during this process, and the temperature was controlled to be 0° C.-15° C. The resulting aqueous phase, separated from the liquids, was extracted once with butan-1-ol (25 ml), to remove most of the impurities by extraction. Then adjusted by 37% HCl to pH=3, and stirred for about 30 minutes. The white solid was precipitated, collected by filtration and drip washed once with methylene chloride (25 mL). Then the precipitated solid was slurried with 15 mL methylene chloride, and stirred for 10 minutes at 25° C. Finally, the white solid (S)—N-Boc-4-borono-L-phenylalanine was obtained by filtration (3.4 g, analyzed by HPLC, 85.26% yield, 98% purity).

The bis(2-dimethylaminoethyl)ether is the complexing agent of Mg, which can reduce the occurrence of side reaction in the reaction. Embodiments 6 and 7 can also carry out the reactions smoothly, without the addition of bis(2-dimethylaminoethyl)ether. By analysis, in the reaction of Embodiment 6, the iodine-dropped impurity is about 17%, and in the reaction of Embodiment 7, the iodine-dropped impurity is about 28%. Therefore, it is laterally demonstrated that, the addition of bis(2-dimethylaminoethyl)ether to the reaction can protect the reaction and reduce the drop of iodine.

The obtained BPA or [10]BPA in the above Embodiments was analyzed by chiral HPLC, indicating the ratio of L to D isomers to be 100 to 0 (100% enantiomeric excess).

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A method for preparing L-BPA comprises steps of:
    reacting N-protected (S)-4-halophenylalanine of Formula I, a boronating agent, Grignard reagent and bis(2-dimethylaminoethyl)ether to obtain a reaction mixture, wherein the $R^1$ group of N-protected (S)-4-halophenylalanine of Formula I is iodide or bromide, the Grignard reagent is tert-butylmagnesium chloride (t-BuMgCl), the reaction mixture comprises N-protected (S)-4-boronophenylalanine of Formula II and the $R^2$ group represents a protecting group;

Formula I

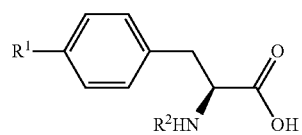

Formula II

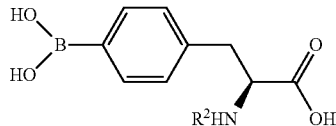

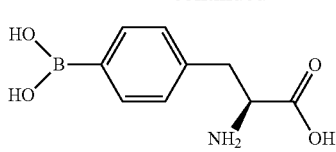

Formula III isolating the N-protected (S)-4-boronophenylalanine from the reaction mixture; and deprotecting the $R^2$ group of the N-protected (S)-4-boronophenylalanine to obtain L-BPA, wherein the L-BPA has a structure of Formula III.

2. The method according to claim 1, wherein the $R^2$ group of N-protected (S)-4-halophenylalanine of Formula I and N-protected (S)-4-boronophenylalanine of Formula II is selected from the group consisting of: tert-butoxycarbonyl (t-Boc) group, trityl (Trt) group, 3,5-dimethoxyphenylisopropoxycarbonyl (Ddz) group, 2-(4-Biphenyl)isopropoxycarbonyl (Bpoc) group, and 2-nitrophenylsulfenyl (Nps) group, the boronating agent is trialkyl borate.

3. The method according to claim 1, wherein the step of reacting N-protected (S)-4-halophenylalanine of Formula I, a boronating agent, Grignard reagent and bis(2-dimethylaminoethyl)ether to obtain a reaction mixture comprises reacting N-protected (S)-4-halophenylalanine of Formula I, a boronating agent, Grignard reagent and bis(2-dimethylaminoethyl)ether at a temperature ranging from 0° C. to 60° C. to obtain the reaction mixture.

4. The method according to claim 1, wherein the step of deprotecting the $R^2$ group of the N-protected (S)-4-boronophenylalanine to obtain L-BPA comprises deprotecting the $R^2$ group of the N-protected (S)-4-boronophenylalanine at a temperature ranging from 30° C. to 60° C. to obtain L-BPA.

5. The method according to claim 1, wherein the boronating agent has a $^{10}B$ purity not less than 95%, the N-protected (S)-4-boronophenylalanine is N-protected (S)-4-($^{10}B$)boronophenylalanine of Formula IV and the L-BPA is L-$^{10}BPA$ of Formula V

Formula IV

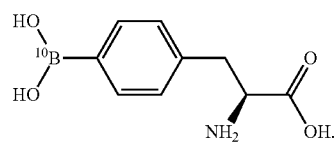

Formula V

6. The method according to claim 1, wherein the method for preparing L-BPA further comprises a step of:

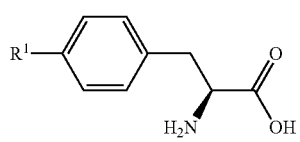

Formula VI protecting the amine terminal of (S)-4-halophenylatermilanine of Formula VI to obtain N-protected (S)-4-halophenylalanine of Formula I.

7. The method according to claim 6, wherein the step of protecting the amine terminal of (S)-4-halophenylalanine of Formula VI to obtain N-protected (S)-4-halophenylalanine of Formula I comprises:

adding the (S)-4-halophenylalanine, 1,4-dioxane, water, sodium hydroxide and di-t-butyl dicarbonate into reaction vessel to perform the reaction;

adjusting the pH value to less than 2 to crystallize the N-protected (S)-4-boronophenyl alanine;

adding a first extractive solvent so as to obtain N-protected (S)-4-boronophenylalanine.

8. The method according to claim 2, wherein trialkyl borate is tributyl borate, the method of preparing L-BPA further comprises a step of reacting the boronic acid with sulfuric acid and butan-1-ol in a first organic solvent, to prepare the tributyl borate.

9. The method according to claim 1, wherein the step of isolating the N-protected (S)-4-boronophenylalanine from the reaction mixture comprises:

adding an organic solvent and acid solution into the reaction mixture, adjusting pH value to less than 5, and extractive, to obtain organic phase;

adding alkaline solution to said organic phase, adjusting the pH value to 7.1-14;

adding an extractive solvent so as to obtain the N-protected (S)-4-boronophenylalanine.

10. The method according to claim 1, wherein the step of deprotecting the $R^2$ group of the N-protected (S)-4-boronophenylalanine to obtain L-BPA comprises:

adding the N-protected (S)-4-borono-L-phenylalanine, water, acid solution and an organic solvent into a reaction vessel;

adjusting the pH value to 6.15-6.25 so as to obtain L-BPA.

11. A method for preparing L-BPA comprises steps of:

reacting N-protected (S)-4-halophenylalanine of Formula I, a boronating agent and Grignard reagent to obtain a reaction mixture, wherein the $R^1$ group of N-protected (S)-4-halophenylalanine of Formula I is iodide or bromide, the Grignard reagent is tert-butylmagnesium chloride (t-BuMgCl), the reaction mixture comprises N-protected (S)-4-boronophenylalanine of Formula II and the $R^2$ group represents a protecting group;

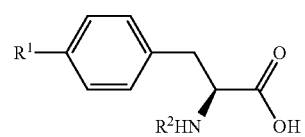

Formula I

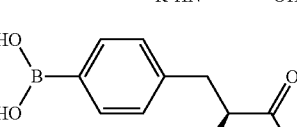

Formula II

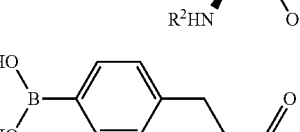

Formula III isolating the N-protected (S)-4-boronophenylalanine from the reaction mixture; and deprotecting the $R^2$ group of the N-protected (S)-4-boronophenylalanine to obtain L-BPA, wherein the L-BPA has a structure of Formula III.

12. The method according to claim 11, wherein the $R^2$ group of N-protected (S)-4-halophenylalanine of Formula I and N-protected (S)-4-boronophenylalanine of Formula II is selected from the group consisting of: tert-butoxycarbonyl (t-Boc) group, trityl (Trt) group, 3,5-dimethoxyphenylisopropoxycarbonyl (Ddz) group, 2-(4-Biphenyl)isopropoxycarbonyl (Bpoc) group, and 2-nitrophenylsulfenyl (Nps) group, the boronating agent is trialkyl borate.

13. The method according to claim 11, wherein the step of reacting N-protected (S)-4-halophenylalanine of Formula I, a boronating agent and Grignard reagent to obtain a reaction mixture comprises reacting N-protected (S)-4-halophenylalanine of Formula I, a boronating agent and Grignard reagent at a temperature ranging from 0° C. to 30° C. to obtain the reaction mixture.

14. The method according to claim 11, wherein the boronating agent has a $^{10}B$ purity not less than 95%, the N-protected (S)-4-boronophenylalanine is N-protected (S)-4-($^{10}B$)boronophenylalanine of Formula IV and the L-BPA is L-$^{10}$ BPA of Formula V

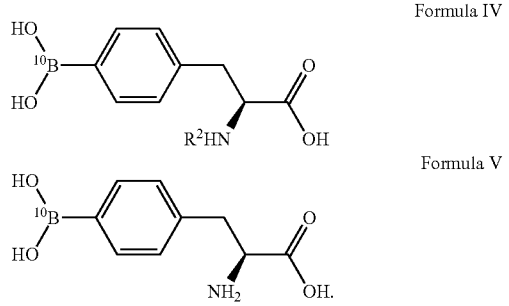

15. A method for preparing L-BPA comprises steps of:
reacting N-protected (S)-4-halophenylalanine of Formula I, a boronating agent, Grignard reagent and bis(2-dimethylaminoethyl)ether to obtain a reaction mixture, wherein the Grignard reagent is tert-butylmagnesium chloride (t-BuMgCl), the reaction mixture comprises N-protected (S)-4-boronophenylalanine of Formula II and the $R^2$ group represents a protecting group;

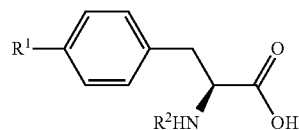

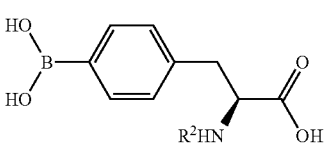

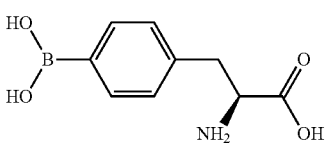

isolating the N-protected (S)-4-boronophenylalanine from the reaction mixture; and deprotecting the $R^2$ group of the N-protected (S)-4-boronophenylalanine to obtain L-BPA, wherein the L-BPA has a structure of Formula III;

wherein the $R^1$ group of N-protected (S)-4-halophenylalanine of Formula I is iodide or bromide, the $R^2$ group of N-protected (S)-4-halophenylalanine of Formula I and N-protected (S)-4-boronophenylalanine of Formula II is selected from the group consisting of: tert-butoxycarbonyl (t-Boc) group, trityl (Trt) group, 3,5-dimethoxyphenylisopropoxycarbonyl (Ddz) group, 2-(4-Biphenyl)isopropoxycarbonyl (Bpoc) group, and 2-nitrophenylsulfenyl (Nps) group, the boronating agent is trialkyl borate.

16. The method according to claim 15, wherein the step of reacting N-protected (S)-4-halophenylalanine of Formula I, a boronating agent, Grignard reagent and bis(2-dimethylaminoethyl)ether to obtain a reaction mixture comprises reacting N-protected (S)-4-halophenylalanine of Formula I, a boronating agent, Grignard reagent and bis(2-dimethylaminoethyl)ether at a temperature ranging from 0° C. to 60° C. to obtain the reaction mixture.

17. The method according to claim 15, wherein the $R^1$ group of N-protected (S)-4-halophenylalanine of Formula I is iodide.

* * * * *